United States Patent [19]

Plath et al.

[11] Patent Number: 5,723,415
[45] Date of Patent: Mar. 3, 1998

[54] 5-HYDROXYPYRAZOL-4-YLCARBONYL-SUBSTITUTED SACCHARIN DERIVATIVES

[75] Inventors: Peter Plath, Frankenthal; Wolfgang von Deyn, Neustadt; Stefan Engel, Wörrstadt; Uwe Kardorff, Mannheim; Hartmann König, Heidelberg; Harald Rang, Altrip; Matthias Gerber, Limburgerhof; Helmut Walter, Obrigheim; Karl-Otto Westphalen, Speyer, all of Germany

[73] Assignee: BASF Aktiengesellschaft, Ludwigshafen, Germany

[21] Appl. No.: 776,576

[22] PCT Filed: Jul. 27, 1995

[86] PCT No.: PCT/EP95/02974

§ 371 Date: Feb. 3, 1997

§ 102(e) Date: Feb. 3, 1997

[87] PCT Pub. No.: WO96/05197

PCT Pub. Date: Feb. 22, 1996

[30] Foreign Application Priority Data

Aug. 8, 1994 [DE] Germany .................. 44 27 997.3

[51] Int. Cl.⁶ .................. A01N 43/80; C07D 417/06
[52] U.S. Cl. .................. 504/269; 548/210
[58] Field of Search .................. 548/210; 504/269

[56] References Cited

U.S. PATENT DOCUMENTS

| | | | |
|---|---|---|---|
| 4,006,007 | 2/1977 | Bollinger et al. | 504/269 X |
| 4,146,726 | 3/1979 | Konotsune et al. | 548/369.4 |
| 4,410,353 | 10/1983 | Theissen | 504/269 |
| 5,306,818 | 4/1994 | Subramanyam et al. | 544/135 |

FOREIGN PATENT DOCUMENTS

| | | | |
|---|---|---|---|
| 323869 | 7/1989 | European Pat. Off. | 548/210 |
| 36 07 343 | 3/1986 | Germany . | |

OTHER PUBLICATIONS

Chem. Abst., vol. 98, No. 15, AN 125661W, 1983.
Derwent Abstract of BE 768172 (Dec. 7, 1971).
Derwent Abstract of JP 73-035,457 (Oct. 27, 1973).
Derwent Abstract of JP 57-016,867 (Jan. 28, 1982).

Primary Examiner—Fiona T. Powers
Attorney, Agent, or Firm—Keil & Weinkauf

[57] ABSTRACT

5-Hydroxypyrazol-4-ylcarbonyl-substituted saccharin derivatives of the formula I

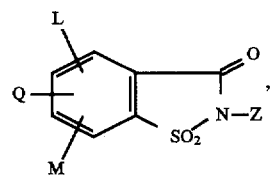

where the substituents have the following meanings:

L and M are hydrogen, $C_1$–$C_4$-alkyl, $C_1$–$C_4$-alkoxy, $C_1$–$C_4$-alkylthio, chlorine, cyano, methylsulfonyl, nitro or trifluoromethyl;

Z is hydrogen, $C_1$–$C_4$-alkyl, $C_3$–$C_8$-cycloalkyl, $C_3$–$C_6$-alkenyl, $C_3$–$C_5$-alkynyl, $C_1$–$C_4$-acyl, benzyl or phenyl, the phenyl rings in each case being unsubstituted or substituted by halogen or $C_1$–$C_4$-alkyl;

Q is a radical CO—J,

J is a 4-linked 5-hydroxypyrazole ring of the formula II

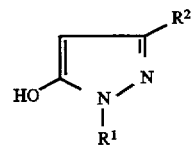

where $R^1$ is $C_1$–$C_4$-alkyl and $R^2$ is hydrogen or methyl, and agriculturally customary salts of the compounds I are described.

6 Claims, No Drawings

5-HYDROXYPYRAZOL-4-YLCARBONYL-SUBSTITUTED SACCHARIN DERIVATIVES

This application is a 371 of PCT/EP95/02974 filed Jul. 27, 1995.

The present application relates to 5-hydroxypyrazol-4-ylcarbonyl-substituted saccharin derivatives of the formula I

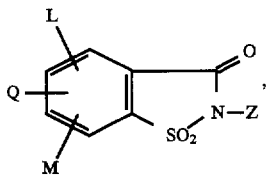

where the substituents have the following meanings:

L and M are hydrogen, $C_1$–$C_4$-alkyl, $C_1$–$C_4$-alkoxy, $C_1$–$C_4$-alkylthio, chlorine, cyano, methylsulfonyl, nitro or trifluoromethyl;

Z is hydrogen, $C_1$–$C_4$-alkyl, $C_3$–$C_8$-cycloalkyl, $C_3$–$C_6$-alkenyl, $C_3$–$C_5$-alkynyl, $C_1$–$C_4$-acyl or benzyl or phenyl, each of which is unsubstituted or substituted by halogen or $C_1$–$C_4$-alkyl;

Q is a radical CO—J,

J is a 4-linked 5-hydroxypyrazole ring of the formula II

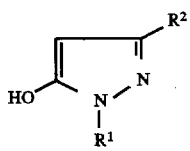

where $R^1$ is $C_1$–$C_4$-alkyl and $R^2$ is hydrogen or methyl, and agriculturally customary salts of the compounds I.

The invention further relates to herbicidal compositions, containing the Compounds I, and methods of controlling undesired plant growth using the saccharin derivatives I.

Saccharin derivatives having herbicidal action cannot be inferred from the prior art. However, unsubstituted saccharin (o-sulfobenzimide, ie. L, M, Q and Z in formula I=H) has been known as a synthetic sweetener for a long time. 4-Hydroxysaccharin is further known as a sweetener (German Offenlegungsschrift 3 607 343). The use of saccharin derivatives in pest control is also known, eg. JP Publication 72/00419, 73/55457 (fungicides) and in pharmacy, eg. EP-A 594 257 and patents further mentioned therein. Heterocyclic compounds having a sulfonamide-containing ring have been disclosed as herbicides, a typical representative which can be mentioned here being bentazone

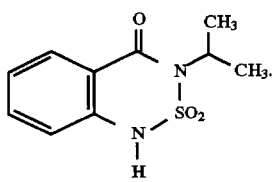

It is an object of the present invention to make available novel herbicides having a basic structure which was hitherto unknown for this indication.

We have found that this object is achieved by the compounds I defined at the outset.

Compounds of the formula I are obtained by acylating 5-hydroxypyrazoles of the formula II with an acid chloride of the formula IV and rearranging the pyrazole ester formed to give saccharin derivatives of the formula I.1,

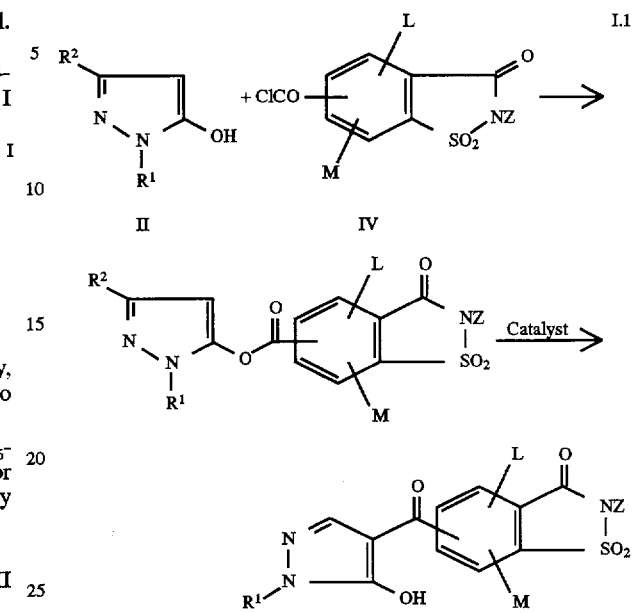

In the abovementioned formulae, L, M and Z have the meanings given at the outset.

The first step of the reaction sequence, the acylation, is carried out in a generally known manner, eg. by addition of an acid chloride of the formula IV to the solution or suspension of a 5-hydroxypyrazole II in the presence of an auxiliary base. The reactants and the auxiliary base are in this case expediently employed in approximately equimolar amounts. A small excess of the auxiliary base, eg. from 1.2 to 1.5 mol equivalents, based on II, can be advantageous in certain circumstances.

Suitable auxiliary bases are tertiary alkylamines, pyridine or alkali metal carbonates, while the solvents used can be eg. methylene chloride, diethyl ether, toluene or ethyl acetate. During the addition of the acid chloride, the reaction mixture is preferably cooled to 0°–10° C., then stirred at higher temperature, eg. at 25°–50° C., until the reaction is complete.

Working up is carried out in a customary manner, eg. the reaction mixture is poured into water and extracted with methylene chloride. After drying the organic phase and removing the solvent, the crude 5-hydroxypyrazole ester can be employed for the rearrangement without further purification. Preparation examples for benzoic acid esters of 5-hydroxypyrazoles are found eg. in EP-A 282 944 or U.S. Pat. No. 4,643,757.

The rearrangement of the 5-hydroxypyrazole esters to the compounds of the formula I.1 is expediently carried out at from 20° C. to 40° C. in a solvent and in the presence of an auxiliary base, and with the aid of a cyano compound as a catalyst. The solvents used can be eg. acetonitrile, methylene chloride, 1,2-dichloroethane, ethyl acetate or toluene. The preferred solvent is acetonitrile. Suitable auxiliary bases are tertiary alkylamines, pyridine or alkali metal carbonates, which are employed in an equimolar amount or an up to four-fold excess. A preferred auxiliary base is triethylamine in a doubled amount. Suitable catalysts are cyanide compounds such as potassium cyanide or acetone cyanohydrin, eg. in an amount of from 1 to 50, in particular 5–20, mol %, based on the 5-hydroxypyrazole ester. Acetone cyanohydrin is preferably added, eg. in amounts of 10 mol %.

Examples of the rearrangement of benzoic acid esters of 5-hydroxypyrazoles are found eg. in EP-A 282 944 or U.S. Pat. No. 4,643,757, but there only potassium carbonate or sodium carbonate in dioxane is used as a catalyst. The use of potassium cyanide or acetone cyanohydrin is indeed known in connection with the similar rearrangement of enol esters of cyclohexane-1,3-diones (U.S. Pat. No. 4,695,673), but no examples are known from the literature in which cyanide compounds are particularly highly suitable for the Fries rearrangement of O-acyl derivatives of 5-hydroxypyrazole.

Working up is carried out in a customary manner, eg. the reaction mixture is acidified with dilute mineral acids such as 5% hydrochloric acid or sulfuric acid and extracted, eg. with methylene chloride or ethyl acetate. For purification, the extract is extracted with cold 5–10% strength alkali metal carbonate solution, the final product passing into the aqueous phase. The product of the formula I is precipitated by acidifying the aqueous solution, or extracted again with methylene chloride, dried and then freed from the solvent.

The 5-hydroxypyrazoles of the formula II used as a starting material are known and can be prepared by processes known per se (cf. EP-A 240 001 and J. Prakt. Chem. 315 (1973), 382). 1,3-Dimethyl-5-hydroxypyrazole is a commercially available compound.

The starting substances of the formula IV are prepared in a manner known per se by reaction of the saccharincarboxylic acid III

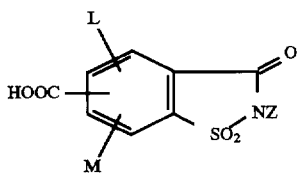

III with thionyl chloride.

Saccharincarboxylic acids III are known in some cases (4-COOH: Zincke, Liebigs Ann. 427 (1922), 231, 5-COOH: Jacobsen, Chem. Ber. 13 (1880), 1554, 6-COOH: Weber, Chem. Ber. 25 (1892), 1740). Further, the preparation of 4-chlorosaccharin-5-carboxylic acid is described in German Offenlegungsschrift 3 607 343.

Saccharincarboxylic acids can also be obtained by reacting corresponding bromo- or iodo-substituted saccharin derivatives of the formula A1

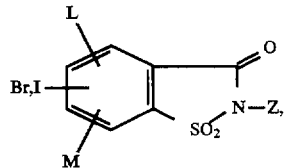

A1 where L, M and Z have the abovementioned meanings, or if Z≠H, compounds of the formula A2

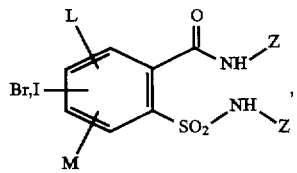

A2 with carbon monoxide and water or a $C_1$–$C_6$-alcohol at elevated pressure in the presence of a palladium, nickel, cobalt or rhodium transition metal catalyst and a base.

Iodosaccharins are already known from the literature: 6-iodosaccharin: De Roode, Amer. Chem. Journal 13 (1891),
231. They are obtained either by permanganate oxidation of iodo-substituted 2-methylbenzenesulfonamides or from aminosaccharins by Sandmeyer reaction. Aminosaccharins are obtained by known methods by reduction of nitrosaccharins, which in turn are either known (Kastle, Amer. Chem. Journal 11 (1889), 184 or DRP 551423. (1930)) or are synthesized in a manner known from the literature from suitable nitrobenzene derivatives (Liebigs Ann. 669 (1963), 85) or nitrobenzenesulfonamides.

If, for example, L is methyl and M and Z are hydrogen, the reaction sequence can be shown as follows:

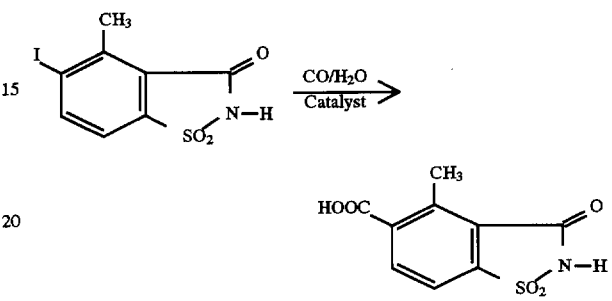

The catalysts nickel, cobalt, rhodium and in particular palladium can be present in metallic form or in the form of customary salts, such as in the form of halogen compounds, eg. $PdCl_2$, $RhCl_3.H_2O$, acetates, eg. $Pd(OAc)_2$, cyanides etc. in the known valency states. Metal complexes with tertiary phosphines, metal alkylcarbonyls, metal carbonyls, eg. $CO_2(CO)_8$, $Ni(CO)_4$, metal carbonyl complexes with tertiary phosphines, eg. $(PPh_3)_2Ni(CO)_2$, or transition metal salts complexed with tertiary phosphines can further be present. The last-mentioned embodiment is particularly preferred in the case of palladium as a catalyst. The nature of the phosphine ligands here is widely variable. For example, they can be represented by the following formulae:

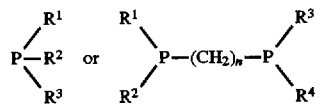

where n is the numbers 1, 2, 3 or 4 and the radicals $R^1$ to $R^4$ are low-molecular weight alkyl, eg. $C_1$–$C_6$-alkyl, aryl or $C_1$–$C_4$-alkylaryl, eg. benzyl, phenethyl or aryloxy. Aryl is, eg. naphthyl, anthryl and preferably unsubstituted or substituted phenyl, it only being necessary with respect to the substituents to take into account their inertness to the carboxylation reaction, otherwise they can be widely varied and include all inert C-organic radicals such as $C_1$–$C_6$-alkyl radicals, eg. methyl, carboxyl radicals such as COOH, COOM (M is eg. an alkali metal, alkaline earth metal or ammonium salt), or C-organic radicals bonded via oxygen, such as $C_1$–$C_6$-alkoxy radicals.

The preparation of the phosphine complexes can be carried out in a manner known per se, eg. as described in the documents mentioned at the outset. For example, customary commercially available metal salts such as $PdCl_2$ or $Pd(OCOCH_3)_2$ are used as starting materials and the phosphine, eg. $P(C_6H_5)_3$, $P(n-C_4H_9)_3$, $PCH_3(C_6H_5)_2$ or 1,2-bis(diphenylphosphino)ethane, is added.

The amount of phosphine, based on the transition metal, is customarily from 0 to 20, in particular from 0.1 to 10, mol equivalents, particularly preferably from 1 to 5 mol equivalents.

The amount of transition metal is not critical. For cost reasons, of course, rather a small amount, eg. from 0.1 to 10 mol %, in particular from 1 to 5 mol %, based on the starting substance A1 or A2, will be used.

Reaction with carbon monoxide and at least equimolar amounts of water, based on the starting substances A1 or A2, is carried out to prepare the saccharincarboxylic acids III. The reaction component water can simultaneously also be used as a solvent, ie. the maximum amount is not critical.

However, it can also be advantageous, depending on the nature of the starting substances and the catalysts used, to use another inert solvent or the base used for the carboxylation as a solvent instead of the reaction component.

Suitable inert solvents for carboxylation reactions are customary solvents such as hydrocarbons, eg. toluene, xylene, hexane, pentane, cyclohexane, ethers, eg. methyl tert-butyl ether, tetrahydrofuran, dioxane, dimethoxyethane, substituted amides such as dimethylformamide, persubstituted ureas such as tetra-$C_1$–$C_4$-alkylureas, or nitriles such as benzonitrile or acetonitrile.

In a preferred embodiment of the process, one of the reaction components, in particular the base, is used in an excess such that no additional solvent is necessary.

Bases suitable for the process are all inert bases which are able to bind the hydrogen iodide or hydrogen bromide liberated in the reaction. Examples which can be mentioned here are tertiary amines such as triethylamine, cyclic amines such as N-methylpiperidine or N,N'-dimethylpiperazine, pyridine, alkali metal or alkaline earth metal hydroxides, carbonates or hydrogen carbonates, or tetraalkyl-substituted urea derivatives such as tetra-$C_1$–$C_4$-alkylurea, eg. tetramethylurea.

The amount of base is not critical, from 1 to 10, in particular from 1 to 5, mol customarily being used. When the base is simultaneously used as a solvent, as a rule the amount is proportioned such that the reaction components are dissolved, unnecessarily high excesses being avoided for reasons of practicability in order to save costs, to be able to employ small reaction vessels and to guarantee maximum contact of the reaction components.

During the reaction, the carbon monoxide pressure is adjusted such that an excess of CO, based on A1 or A2, is always present. Preferably, the carbon monoxide pressure at room temperature is from 1 to 250 bar, in particular from 5 to 150 bar, of CO.

As a rule, the carbonylation is carried out continuously or batchwise at from 20° to 250° C., in particular at from 30° to 150° C. In the case of batchwise operation, carbon monoxide is expediently injected into the reaction mixture continuously to maintain a constant pressure.

The products can be isolated from the resulting reaction mixture in a customary manner, eg. by distillation.

The starting substances A1 and A2 required for the reaction are known or can be prepared in a manner known per se, eg. as described in the cited prior art. Moreover, they can be obtained in a similar manner to the preparation procedures of Examples 1 to 12.

With respect to the intended use, saccharin derivatives of the formula I are preferred where the radicals L and M are hydrogen, methyl, methoxy, methylthio, chlorine, cyano, methylsulfonyl, nitro or trifluoromethyl. Further, L and M are preferably hydrogen, $C_1$–$C_4$-alkyl and chlorine. Compounds I are furthermore preferred where L and M are hydrogen or one of the radicals L or M is hydrogen and the other is methyl or chlorine.

The radical $R^1$ in formula I is preferably methyl and $R^2$ is preferably hydrogen or methyl.

The radical Z is particularly preferably one of the organic radicals mentioned, in particular methyl, ethyl, propargyl, acetyl or phenyl.

Particularly preferred active compounds can be taken from Table 1. The groups mentioned for a substituent in Table 1 are additionally considered per se, independently of the specific combination with other substituents in which they are mentioned, to be a particularly preferred definition of the substituent concerned.

The compounds I can be present in the form of their agriculturally utilizable salts, the nature of the salt in general not mattering. Customarily, the salts of those bases which do not adversely affect the herbicidal action of I will be suitable.

Suitable basic salts are particularly those of the alkali metals, preferably the sodium and potassium salts, those of the alkaline earth metals, preferably calcium, magnesium and barium salts and those of the transition metals, preferably manganese, copper, zinc and iron salts as well as the ammonium salts, which can carry one to three $C_1$–$C_4$-alkyl or hydroxy-$C_1$–$C_4$-alkyl substituents and/or a phenyl or benzyl substituent, preferably diisopropylammonium, tetramethylammonium, tetrabutylammonium, trimethylbenzylammonium and trimethyl-(2-hydroxyethyl)ammonium salts, the phosphonium salts, the sulfonium salts, preferably tri($C_1$–$C_4$)-alkylsulfonium salts, and the sulfoxonium salts, preferably tri($C_1$–$C_4$)-alkylsulfoxonium salts.

The compounds or the herbicidal compositions containing them and their environmentally tolerable salts of, for example, alkali metals, alkaline earth metals or ammonia and amines or the herbicidal compositions containing them can control broad-leaved weeds and grass weeds highly effectively in crops such as wheat, rice, maize, soybeans and cotton without noticeably damaging the crop plants. This effect occurs especially at low application rates.

Taking into account the versatility of the application methods, the compounds or compositions containing them can also be employed in a further number of crop plants for the elimination of undesired plants. Examples of suitable crops are the following: *Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa,* Musa spp., *Nicotiana tabacum (N. rustica), Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.*

Moreover, the compounds can also be employed in crops which have been made largely resistant to the action of I or other herbicides by breeding and/or by means of genetic engineering methods.

The application of the herbicidal compositions or of the active compounds can be carried out preemergence or postemergence. If the active compounds are less tolerable for certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

The compounds or the herbicidal compositions containing them can be applied by spraying, atomizing, dusting, scattering or watering, for example in the form of directly sprayable aqueous solutions, powders, suspensions, even high-percentage aqueous, oily or other suspensions or dispersions, emulsions, oil dispersions, pastes, dusting compositions, scattering compositions or granules. The application forms depend on the intended uses; if possible they should in each case guarantee the finest dispersion of the active compounds according to the invention.

Suitable inert auxiliaries for the preparation of directly sprayable solutions, emulsions, pastes or oil dispersions are essentially: mineral oil fractions of medium to high boiling point such as kerosene or diesel oil, further coal tar oils and oils of vegetable or animal origin, aliphatic, cyclic and aromatic hydrocarbons, e.g. paraffins, tetrahydronaphthalene, alkylated naphthalenes or their derivatives, alkylated benzenes and their derivatives, alcohols such as methanol, ethanol, propanol, butanol and cyclohexanol, ketones such as cyclohexanone or strongly polar solvents, eg. amines such as N-methylpyrrolidone, or water.

Aqueous application forms can be prepared from emulsion concentrates, suspensions, pastes, wettable powders or water-dispersable granules by addition of water. To prepare emulsions, pastes or oil dispersions, the substrates can be homogenized in water, as such or dissolved in an oil or solvent, by means of wetting agents, adhesives, dispersants or emulsifiers. However, concentrates consisting of active substance, wetting agent, adhesive, dispersant or emulsifier and possibly solvent or oil which are suitable for dilution with water can also be prepared.

Suitable surface-active substances are the alkali metal, alkaline earth metal or ammonium salts of aromatic sulfonic acids, eg. lignosulfonic, phenolsulfonic, naphthalenesulfonic and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols as well as of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octyl phenol ethers, ethoxylated isooctyl-, octyl- or nonylphenol, alkylphenyl or tributylphenylpolyglycol ethers, alkylaryl polyether alcohols, isotridecyl alcohol, fatty alcoholethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, scattering and dusting compositions can be prepared by mixing or joint grinding of the active substances with a solid carrier.

Granules, eg. coated, impregnated and homogeneous granules can be prepared by binding of the active compounds to solid carriers. Solid carriers are mineral earths such as silicic acids, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products such as cereal flour, tree bark meal, wood meal and nutshell meal, cellulose powder or other solid carriers.

In general, the formulations contain from 0.01 to 95% by weight, preferably from 0.5 to 90% by weight, of active compound. The active compounds are employed here in a purity of from 90% to 100%, preferably from 95% to 100% (according to NMR spectrum). The compounds I according to the invention can be formulated, for example, as follows:

I. 20 parts by weight of the compound I are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II. 20 parts by weight of the compound I are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to I mol of castor oil. By pouring the solution into and finely dispersing it in 100,000 parts by weight of water, an aqueous dispersion is obtained which contains 0.02% by weight of the active compound.

III. 20 parts by weight of the active compound I are dissolved in a mixture which consists of 25 parts by weight of cyclohexanone, 65 parts by weight of a mineral oil fraction of boiling point from 210° to 280° C. and 10 parts by weight of the addition product of 40 mol of ethylene oxide to 1 mol of castor oil. By pouring the solution into and finely dispersing it in 100.000 parts by weight of water, an aqueous dispersion is obtained which contains 0.02% by weight of the active compound.

IV. 20 parts by weight of the active compound I are thoroughly mixed with 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel and ground in a hammer mill. By finely dispersing the mixture in 20,000 parts by weight of water, a spray mixture is obtained which contains 0.1% by weight of the active compound.

V. 3 parts by weight of the active compound I are mixed with 97 parts by weight of finely divided kaolin. In this way, a dusting composition is obtained which contains 3% by weight of the active compound.

VI. 20 parts by weight of the active compound I are intimately mixed with 2 parts by weight of calcium salt of dodecylbenzenesulfonic acid, 8 parts by weight of fatty alcohol polyglycol ether, 2 parts by weight of sodium salt of a phenol-urea-formaldehyde condensate and 68 parts by weight of a paraffinic mineral oil. A stable oily dispersion is obtained.

To widen the spectrum of action and to achieve synergistic effects, the saccharincarboxylic acid derivatives can be mixed with numerous representatives of other herbicidal or growth-regulating active compound groups and applied jointly. For example, suitable mixture components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry eg. a carboxyl or carbimino group in the 2-position, quinolinecarboxylic acid derivatives, imidazolinones, sulfonamides, sulfonylureas, aryloxy- or heteroaryloxyphenoxypropionic acids and their salts, esters and amides and others.

Additionally, it may be useful to apply the compounds I on their own or together in combination with other herbicides, additionally mixed with further crop protection agents, for example with agents for controlling pests or phytopathogenic fungi and bacteria. Further of interest is the miscibility with mineral salt solutions, which are employed for the elimination of nutritional and trace element deficiencies. Nonphytotoxic oils and oil concentrates can also be added.

Depending on the aim of control, time of year, target plants and stage of growth, the application rates of active compound are from 0.001 to 3.0, preferably from 0.01 to 1.0, kg/ha of active substance (a.s.).

PREPARATION EXAMPLES 1. 2-Methyl-6-acetamidobenzoic acid 90.6 g (0.6 mol) of 6-methylanthranilic acid are added to a solution of 24.8 g (0.62 mol) of NaOH in 500 ml of water and 63.4 g (0.62 mol) of acetic anhydride are then added dropwise. After stirring for one hour, the mixture is acidified to pH 3 with conc. HCl with cooling, and the precipitate which deposits is filtered off with suction, washed with water and dried under reduced pressure at 50° C.

Yield: 107 g (0.55 mol)=92% of theory, m.p.: 189°–190° C.

2. 2-Methyl-3-nitro-6-acetamidobenzoic acid 271 ml of 98% nitric acid are initially taken at −5° C. and 106 g (0.55 mol) of the 2-methyl-6-acetamidobenzoic acid prepared in 1. are added in portions. After stirring at 10° C. for one hour, the reaction mixture is poured into a mixture of 540 g of ice and 270 ml of water. The deposited precipitate is filtered off with suction, washed with water and dried under reduced pressure at 50° C.

Yield: 75.6 g (0.317 mol)=58% of theory, m.p.: 190°–191° C.

The isomer nitrated in the 3-position is deposited from the filtrate after relatively long standing:

Yield: 21.3 g (0.089 mol)=16% of theory, m.p.: 180°–182° C.

3. 2-Methyl-3-nitro-6-aminobenzoic acid 450 ml of 2N NaOH are initially taken and 75.6 g (0.317 mol) of 2-methyl-3-nitro-6-acetamidobenzoic acid are added. The reaction mixture is then warmed to 95° C. and is stirred at this temperature for one hour. After cooling to 10° C., it is acidified by addition of 425 ml of 2N HCl, and the precipitate which deposits is filtered off with suction, washed with water and dried under reduced pressure at 50° C.

Yield: 50.7 g (0.258 mol)=82% of theory, m.p.: 183°–184° C.

4. Methyl 2-methyl-3-nitro-6-aminobenzoate 49.7 g (0.253 mol) of 2-methyl-3-nitro-6-aminobenzoic acid are dissolved in 380 ml of acetone and 43 g (0.51 mol) of sodium hydrogen carbonate are added. The mixture is then heated to boiling until evolution of $CO_2$ is complete. 35.3 g (0.28 mol) of dimethyl sulfate are then added dropwise in the course of two hours at the boiling point of acetone to the suspension of the sodium salt of 2-methyl-3-nitro-6-aminobenzoic acid thus obtained, and the mixture is subsequently refluxed for a further three hours and then allowed to cool. After pouring the reaction mixture into 1.8 l of water, it is extracted with methylene chloride. After drying the organic phase, it is concentrated. The solid obtained is sufficiently pure for the subsequent reaction (NMR).

Yield: 50 g (0.238 mol)=94% of theory, m.p.: 92°–94° C.

5. 2-Methoxycarbonyl-3-methyl-4-nitrobenzenesulfonyl chloride 58.5 g (0.278 mol) of methyl 2-methyl-3-nitro-6-aminobenzoate are dissolved with warming in 280 ml of glacial acetic acid and this solution is poured at 15°–20° C. into 85 ml of conc. HCl. A solution of 19.3 g (0.28 mol) of sodium nitrite in 60 ml of water is then added dropwise at 5°–10° C. and the mixture is stirred at 5° C. for 30 min. This diazonium salt solution is subsequently added dropwise to a solution of 374 g of $SO_2$ in 750 ml of glacial acetic acid which contains 14 g of $CuCl_2$ (dissolved in 30 ml of water). After completion of the evolution of nitrogen, the mixture is stirred for a further 15 min and then poured into 1.4 l of ice-water. The sulfonyl chloride is separated off by extraction with 1.2 l of methylene chloride. After drying and concentrating the organic phase, 73 g (0.25 mol) (=90% of theory) of an oil are obtained, which according to NMR (in $CDCl_3$) is pure 2-methoxycarbonyl-3-methyl-4-nitrobenzenesulfonyl chloride.

6. 4-Methyl-5-nitrosaccharin 104 ml of 25% ammonia solution are initially taken, 100 ml of water are added and a solution of 48.7 g (0.166 mol) of 2-methoxycarbonyl-3-methyl-4-nitrobenzenesulfonyl chloride in 70 ml of tetrahydrofuran is then added dropwise at 10° C. After stirring at 25° C. for three hours, the mixture is concentrated on a rotary evaporator to remove water and THF. The residue which remains is stirred with ethyl acetate, filtered off with suction and washed with ethyl acetate. After drying under reduced pressure, 34 g (0.131 mol)=79% of theory of a white solid of m.p.: 312° C. (dec.) are obtained.

7. 2,4-Dimethyl-5-nitrosaccharin

This substance can be prepared by subsequent methylation of the saccharin obtained in 6. using dimethyl sulfate in the presence of NaOH.

8. 3-Methyl-4-nitro-2-(N'-methyl)carboxamido-N-methylbenzenesulfonamide 50 ml of water are poured into 50 ml of 40% methylamine solution and a solution of 24.3 g (83 mmol.) of 2-methoxycarbonyl-3-methyl-4-nitrobenzenesulfonyl chloride in 35 ml of THF is added dropwise at 10° C. After stirring for one hour at 25° C., all volatile constituents are removed on a rotary evaporator, the residue is extracted with ethyl acetate, and the organic phase is washed with water, dried and concentrated. The residue which remains crystallizes after relatively long standing.

Yield: 10.3 g (40 mmol=48% of theory), m.p.: 125°–126° C., after recrystallization from ethyl acetate m.p.: 144°–145° C.

9. 4-Methyl-5-aminosaccharin 33.6 g (0.13 mol) of 4-methyl-5-nitrosaccharin are dissolved in 1.2 l of water with warming to 45° C. and 5 g of Pd/C (10% on active carbon) are added. Hydrogen gas is then passed in with vigorous stirring (pressureless hydrogenation). 9 l of $H_2$ are absorbed in the course of 4.5 hours. After cooling to 25° C., the catalyst is filtered off, and the filtrate is concentrated to a volume of 200 ml and then acidified to pH 1. The deposited precipitate is filtered off with suction, washed with water and dried under reduced pressure at 50° C. 23.4 g (0.11 mol=85% of theory) of a white solid of m.p.: 272°–273° C. are obtained.

10. 4-Methyl-5-iodosaccharin

A mixture of 205 ml of glacial acetic acid, 160 ml of water and 40 ml of conc. HCl is initially taken and 23.4 g (0.11 mol) of 4-methyl-5-aminosaccharin are introduced with stirring at 15°–20° C. 7.9 g (0.115 mol) of sodium nitrite are added dropwise to the resulting suspension at 5°–10° C. and it is stirred at 5° C. for 30 min. The diazonium salt, which is present as a suspension, is then added dropwise in portions to a solution of 19.1 g (0.115 mol) of potassium iodide in 170 ml of water which is warmed to 50° C., nitrogen being formed. After cooling to room temperature, the deposited product is isolated by filtering off with suction, washed with water and dried under reduced pressure at 50° C. 32.5 g (0.1 mol=91% of theory) of a solid of m.p.: 257°–258° C. are obtained. A combustion analysis gave an iodine content of 38.5% (theory 39.3%).

The product is sufficiently pure for the subsequent reaction.

11. 4-Methylsaccharin-5-carboxylic acid 6.4 g (0.002 mol) of 4-methyl-5-iodosaccharin are dissolved in 70 ml of tetramethylurea and 30 ml of water and treated with 0.7 g of bis(triphenylphosphine)palladium chloride and the mixture is heated to 100° C. in a 300 ml autoclave and stirred at a pressure of 100 bar of carbon monoxide for 36 h.

For working up, the mixture is filtered, and water and tetramethylurea are removed by distillation in a high vacuum. The residue is taken up in methyl tert-butyl ether (MTBE), extracted with $NaHCO_3$ soln. and, after acidifying with HCl, extracted again with MTBE. After concentrating, 2.8 g of 4-methylsaccharin-5-carboxylic acid (58% of theory) are obtained.

$^1$H NMR (DMSO, 400.1 MHz): 2.85 (3H, s); 8.05 (1H, d); 8.2 (1H, d);

$^{13}$C NMR (DMSO, 100.6 MHz): 167.4 (CO); 161.3 (CO); 141.6 (quart. C); 139.7 (quart. C); 138.7 (quart. C); 135.6 (CH); 125.4 (quart. C); 118.5 (CH); 15.4 ($CH_3$).

12. 2,4-Dimethylsaccharin-5-carboxylic acid 7.3 g (0.02 mol) of 3-methyl-4-iodo-2-(N'-methyl) carboxamido-N-methylbenzenesulfonamide are initially taken in a 300 ml autoclave, together with 0.69 g of bis(triphenylphosphine)palladium chloride, 30 ml of water and 70 ml of tetramethylurea, and the mixture is heated to 100° C. and stirred at a pressure of 100 bar of carbon monoxide for 36 h.

After working up as described in Example 12, 4.1 g of the title compound are obtained (0.014 mol=72% of theory).

$^1$H NMR (DMSO, 400.1 MHz): 2.9 (3H, s); 3.15 (3H, s); 8.2 (2H, 2d); 14.0 (1H, s)

$^{13}$C NMR (DMSO, 100.6 MHz): 167.3 (CO); 158.6 (CO); 139.7 (quart. C); 139.1 (quart. C); 138.9 (quart. C); 135.5 (CH); 124.6 (quart. C); 119.0 (CH); 22.9 ($CH_3$); 15.6 ($CH_3$).

13. 4-Amino-3-methyl-2-(N'-methyl)carboxamido-N-methylbenzenesulfonamide

In a similar manner to the procedure described in section 9, the 3-methyl-4-nitro-2-(N'-methyl)carboxamido-N-methylbenzenesulfonamide obtained in section 8 was hydrogenated without pressure.

The aniline derivative of the following structure of m.p. 217°–218° C. is obtained in 93% yield.

14. 3-Methyl-4-iodo-2-(N'-methyl) carboxamido-N-methylbenzenesulfonamide

The above compound was diazotized according to the procedure described in section 10 and converted to the iodobenzene derivative of the structure by reaction with KI.

Yield: 95%, m.p.: 60°–62° C.

15. 2,4-Dimethylsaccharin-5-carbonyl chloride 3.8 g (14.9 mmol) of 2,4-dimethylsaccharin-5-carboxylic acid are suspended in 100 ml of toluene, and the mixture is warmed to 80° C. and 3.5 g (29.8 mmol) of thionyl chloride are added dropwise. After refluxing for two hours, the solution is decanted hot and the reaction mixture is concentrated on a rotary evaporator. The product obtained (3 g, 74% of theory) has m.p.: 149°–150° C.

16. General Procedure for the Preparation of the Compounds I

16.1 Acylation of 5-hydroxy-1,3-dimethylpyrazole with a saccharincarbonyl chloride 1.01 g (11 mmol) of triethylamine are added to a suspension of 1.12 g (10 mmol) of 5-hydroxy-1,3-dimethylpyrazole in 70 ml of methylene chloride. A solution or suspension of 10 mmol of the acid chloride of the formula IV in 30 ml of methylene chloride is then added dropwise at 25° C. and the reaction mixture is then warmed to 45° C. for 5 hours. After cooling to 25° C., it is treated with 60 ml of water and poured into a separating funnel, and the organic phase is separated off. After extraction of the aqueous phase with 50 ml of methylene chloride, the organic phases are combined and dried over sodium sulfate. After filtering and removing the methylene chloride, an oil remains which is used without further purification for the rearrangement.

16.2 Rearrangement of the Pyrazole Ester Obtained in 16.1

The saccharincarboxylic acid O-acyl ester of 5-hydroxy-1,3-dimethylpyrazole (about 10 mmol) obtained in 16.1 is initially taken in 80 ml of acetonitrile and first treated with 2.7 ml (2.2 g=20 mmol) of triethylamine, then with 0.2 g (2.3 mmol) of acetone cyanohydrin and the reaction mixture is stirred at 25° C. for 16 hours. 30 g of 5% HCl are then poured into the reaction mixture and it is extracted with methylene chloride. The organic phase is then extracted with 5% potassium carbonate solution, the organic phase is discarded and the alkaline-aqueous phase is acidified to pH 1 by dropwise addition of conc. HCl, the product precipitating as a viscous mass. For purification, the product is dissolved in methylene chloride, and the solution is washed with water, dried over sodium sulfate and concentrated. By rubbing with diethyl ether/petroleum ether, the residue becomes crystalline. The compounds compiled in Table 1 can be obtained in a similar manner:

TABLE 1

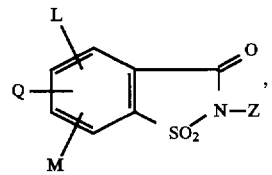

| No. | $R^1$ | $R^2$ | Q-Pos. | L | M | Z | M.p. (°C.) |
|---|---|---|---|---|---|---|---|
| 1.01 | $CH_3$ | H | 4 | H | H | H | |
| 1.02 | $CH_3$ | $CH_3$ | 4 | H | H | H | |
| 1.03 | $C_2H_5$ | H | 4 | H | H | $CH_3$ | |
| 1.04 | $CH_3$ | H | 4 | H | H | $C_2H_5$ | |
| 1.05 | $CH_3$ | H | 4 | H | H | $C_6H_5$ | |
| 1.06 | $CH_3$ | H | 5 | 4-$CH_3$ | H | H | |
| 1.07 | $CH_3$ | H | 5 | 4-Cl | H | H | |
| 1.08 | $CH_3$ | $CH_3$ | 5 | H | 4-$CH_3$ | $CH_3$ | |
| 1.09 | $CH_3$ | $CH_3$ | 5 | H | 4-Cl | $C_2H_5$ | |
| 1.10 | $C_2H_5$ | H | 5 | H | H | Propargyl | |
| 1.11 | $CH_3$ | H | 6 | H | H | $CH_3$ | |
| 1.12 | $CH_3$ | H | 6 | 4-$CH_3$ | H | H | |
| 1.13 | $CH_3$ | H | 6 | 4-Cl | H | H | |
| 1.14 | $CH_3$ | $CH_3$ | 6 | H | 4-$CH_3$ | $CH_3$ | |
| 1.15 | $CH_3$ | $CH_3$ | 6 | H | 4-Cl | $CH_3$ | |

USE EXAMPLES

It was possible to show the herbicidal action of the saccharin derivatives of the formula I by greenhouse tests:

The cultivation vessels used were plastic flowerpots containing loamy sand with about 3.0% humus as a substrate. The seeds of the test plants were sown separately according to species.

In the case of preemergence treatment, the active compounds suspended or emulsified in water were applied directly after sowing by means of finely dispersing nozzles. The vessels were lightly watered in order to promote germination and growth, and then covered with transparent plastic hoods until the plants had taken root. This covering causes a uniform germination of the test plants if this was not adversely affected by the active compounds.

For the purpose of postemergence treatment, the test plants were first raised, according to growth form, to a height of growth of from 3 to 15 cm and only then treated with the active compounds suspended or emulsified in water. For this purpose, the test plants were either sown directly and raised in the same vessels or they were first raised separately as seedlings and transplanted into the test vessels a few days before the treatment.

The plants were kept species-specifically at 10°–25° C. or 20°–35° C. The test period extended over 2 to 4 weeks. During this time, the plants were tended and their reaction to the individual treatments was assessed.

Rating was carried out on a scale of from 0 to 100. 100 in this case means no emergence of the plants or complete destruction of at least the above-ground parts and 0 means no damage or normal course of growth.

We claim:

1. A 5-hydroxypyrazol-4-ylcarbonyl-substituted saccharin derivative of the formula I

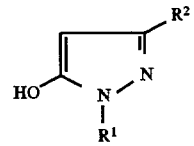

where the substituents have the following meanings:

L and M are hydrogen, $C_1$–$C_4$-alkyl, $C_1$–$C_4$-alkoxy, $C_1$–$C_4$-alkylthio, chlorine, cyano, methylsulfonyl, nitro or trifluoromethyl;

Z is hydrogen, $C_1$–$C_4$-alkyl, $C_3$–$C_8$-cycloalkyl, $C_3$–$C_6$-alkenyl, $C_3$–$C_5$-alkynyl, $C_1$–$C_4$-acyl, benzyl or phenyl, the phenyl rings in each case being unsubstituted or substituted by halogen or $C_1$–$C_4$-alkyl;

Q is a radical CO—J,

J is a 4-linked 5-hydroxypyrazole ring of the formula II

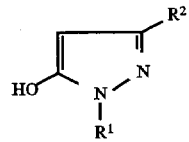

where $R^1$ is $C_1$–$C_4$-alkyl and $R^2$ is hydrogen or methyl, and agriculturally customary salts of the compounds I.

2. A saccharin derivative of the formula I as claimed in claim 1, where the radicals L and M are hydrogen, $C_1$–$C_4$-alkyl or chlorine.

3. A saccharin derivative of the formula I as claimed in claim 1, where the radicals L and M are hydrogen, methyl, methoxy, methylthio, chlorine, cyano, methylsulfonyl, nitro or trifluoromethyl.

4. A herbicidal composition, containing at least one saccharin derivative of the formula I as claimed in claim 1 and customary inert additives.

5. A method of controlling undesired plant growth, which comprises allowing a herbicidally active amount of a saccharin derivative of the formula I as claimed in claim 1 to act on the plants or their habitat.

6. A process for preparing the compounds of the formula I as claimed in claim 1, which comprises acylating 5-hydroxypyrazoles of the formula II where $R^1$ is $C_1$–$C_4$-alkyl and $R^2$ is hydrogen or methyl, with an acid chloride of the formula IV
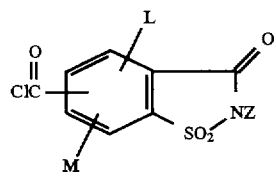
IV
where L, M and Z have the meanings mentioned in claim 1, and rearranging the acylation product to the compounds I in the presence of a catalyst.
* * * * *